(12) United States Patent
Zierenberg et al.

(10) Patent No.: US 7,665,461 B2
(45) Date of Patent: Feb. 23, 2010

(54) NEBULIZER

(75) Inventors: Bernd Zierenberg, Bingen (DE);
Gilbert Wuttke, Dortmund (DE);
Michael Schyra, Wuppertal (DE);
Guido Schmiedel, Dortmund (DE);
Hubert Kunze, Dortmund (DE);
Matthias Hausmann, Dortmund (DE);
Christian Golberg, Gelsenkirchen (DE);
Johannes Geser, Ingelheim (DE);
Andreas Fiol, Norderstedt (DE)

(73) Assignee: Boehringer Ingelheim International GmbH, Ingelheim (DE)

( * ) Notice: Subject to any disclaimer, the term of this patent is extended or adjusted under 35 U.S.C. 154(b) by 845 days.

(21) Appl. No.: 11/064,628

(22) Filed: Feb. 24, 2005

(65) Prior Publication Data
US 2006/0027233 A1    Feb. 9, 2006

(30) Foreign Application Priority Data
Feb. 24, 2004  (DE) ................ 10 2004 009 434

(51) Int. Cl.
*A61M 11/00* (2006.01)
(52) U.S. Cl. .................. 128/200.21; 128/200.14
(58) Field of Classification Search ............ 128/200.14, 128/200.21, 200.11, 203.12
See application file for complete search history.

(56) References Cited

U.S. PATENT DOCUMENTS

| 5,218,983 | A  | * | 6/1993  | King ......................... 137/1 |
| 5,255,823 | A  |   | 10/1993 | Tichy et al. |
| 5,277,334 | A  |   | 1/1994  | Malinconico |
| 5,335,823 | A  |   | 8/1994  | Fuchs et al. |
| 5,522,378 | A  | * | 6/1996  | Ritson et al. ......... 128/200.14 |
| 6,595,389 | B2 |   | 7/2003  | Fuchs |
| 6,745,761 | B2 | * | 6/2004  | Christrup et al. ....... 128/200.14 |
| 7,191,777 | B2 | * | 3/2007  | Brand et al. .......... 128/200.23 |
| 2003/0127538 | A1 | * | 7/2003 | Patel et al. ................. 239/338 |

FOREIGN PATENT DOCUMENTS

| WO | 91/14468 A1 | 10/1991 |
| WO | 97/12687 A1 | 4/1997 |

* cited by examiner

*Primary Examiner*—Steven O Douglas
(74) *Attorney, Agent, or Firm*—David S. Safran; Roberts Mlotkowski Safran & Cole, P.C.

(57) ABSTRACT

A nebulizer for a fluid and a container holding the fluid which is insertable in the nebulizer are proposed. To improve safety in use it is proposed that the nebulizer comprises first coding means and the container is associated with second coding means, so that the container can only be inserted in the nebulizer or used therewith if the codes match. Preferably, the code associated with the container comprises clear identification of the fluid contained in the container.

20 Claims, 13 Drawing Sheets

NEBULIZER

BACKGROUND OF THE INVENTION

1. Field of the Invention

The present invention relates to a nebulizer according to the preamble of claim 1 and a container for a nebulizer according to the preamble of claim 15.

2. Description of the Prior Art

The starting point for the present invention is a nebulizer in the form of an inhaler as shown in principle in WO 91/14468 and specifically in WO 97/12687 (FIGS. 6a, 6b) and in FIGS. 1 and 2 of the enclosed drawings. The nebulizer comprises as a reservoir for a fluid which is to be nebulized and insertable container with the fluid and a pressure generator with a drive spring for conveying and atomising the fluid.

WO 91/14468 and WO 97/12687 are hereby incorporated by reference in their entireties. Generally, the disclosure therein preferably refers to a nebulizer having a spring pressure of 5 to 60 MPa, preferably 10 to 50 MPa on the fluid, with volumes per actuation of 10 to 50:1, preferably 10 to 20 μl, most preferably about 15 μl per actuation and particle sizes of up to 20 μm, preferably 30 to 10 μm. Moreover, the disclosure therein preferably relates to a nebulizer with a cylinder-like shape which is about 9 cm to about 15 cm long and about 2 to about 5 cm wide and a nozzle spray spread of from 20° to 160°, preferably from 80° to 100°. These magnitudes also apply to the nebulizer according to the teaching of the invention as particularly preferred values.

By rotating an actuating member in the form of a lower housing part of the nebulizer the drive spring can be put under tension and fluid can be drawn up into a pressure chamber of the pressure generator. After manual actuation of a locking element the fluid in the pressure chamber is put under pressure by the drive spring and nebulized, i.e. expelled to form an aerosol. During the tensioning process and subsequent atomising, on the other hand, the container performs a lifting movement.

The nebulizer comprises a mechanical monitoring device which detects rotation of the actuating member in order to count the actuations of the nebulizer. The known nebulizer operates purely mechanically, i.e. without propellant gas or electricity.

In the known nebulizer, containers with various fluids, i.e. in particular different pharmaceutical compositions, may be used. This can lead to the risk of confusion during use as the nebulizer may be set or intended for the particular fluid, for example, and/or because a container containing the wrong fluid with the wrong concentration of active substance or the wrong quantity may be used by accident, in particular.

SUMMARY OF THE INVENTION

The aim of the present invention is to provide a nebulizer and a container for a nebulizer with improved protection against getting the container mixed up during use.

The objective described above is achieved with a nebulizer according to claim 1 or a container according to claim 15. Advantageous features form the subject of the subsidiary claims.

A fundamental idea of the present invention is to provide a coding so that only one specific container or a number of specific containers can be used with a nebulizer intended for them, particularly can be inserted therein. The nebulizer has first coding means for this purpose. Second coding means are associated with the container. The coding means cooperate so that the container with the associated second coding means can only be inserted in the nebulizer or used therewith when the coding means match or form the correct code.

The proposed solution provides substantially better protection against getting the container mixed up, as the accident or insertion of the wrong container, particularly a container with the wrong fluid, e.g. the wrong drug, the wrong concentration of active substance or the wrong amount, can be ruled out by the coding. In particular, this prevents a nebulizer which is designed for a particular fluid from being wrongly used for a different fluid and leading, for example, to an excessively high dose of a fluid.

Preferably, the coding operates or acts purely mechanically. This provides a very simple and hence inexpensive construction.

Alternatively or additionally, however, the coding may also work electrically, inductively, capacitively, magnetically and/or optically. In particular, because of the coding of the container, a monitoring device can detect which fluid, particularly a pharmaceutical composition, has been inserted.

According to another aspect of the present invention which may also be implemented independently, the container comprises coding means for clearly identifying the container, the fluid, the concentration of an active substance in the fluid and/or the quantity of fluid. This allows identification of the fluid or pharmaceutical composition which is actually being used with the nebulizer so that once again safety during use can be substantially improved. This is particularly applicable when the nebulizer or, for example, a monitoring device of the nebulizer identifies the fluid used by the coding means and, for example, stores, indicates or otherwise processes the identification.

DESCRIPTION OF THE FIGURES

Further advantages, features, properties and aspects of the present invention will become apparent from the following description of preferred embodiments with reference to the drawings, wherein.

In the Figures, identical reference numerals are used for identical or similar parts, and corresponding or comparable properties and advantages are achieved even if the description is not repeated.

DESCRIPTION OF THE INVENTION

Figure 1:
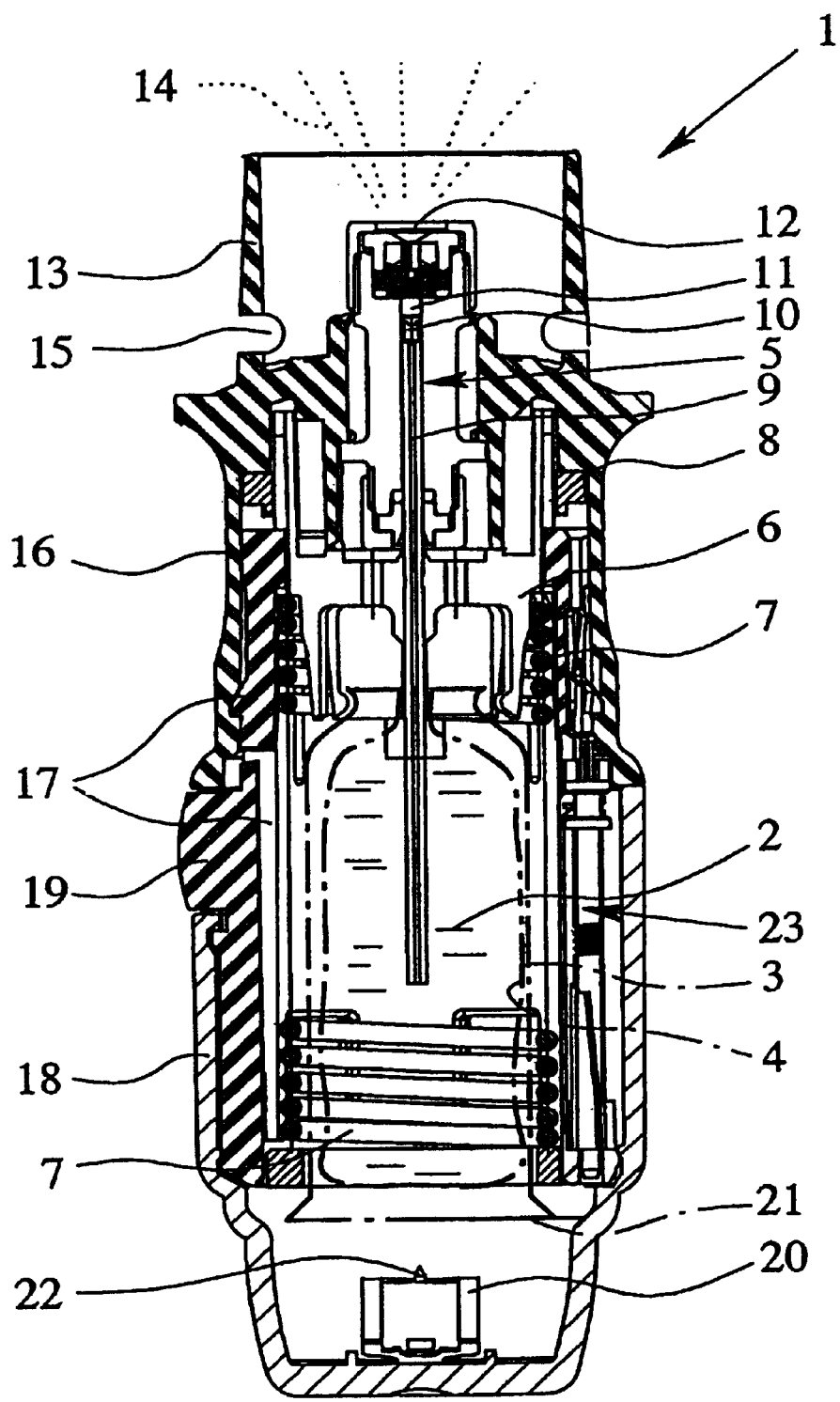
FIG. 1 is a diagrammatic section through a known nebulizer in the untensioned stated.
Figure 2:
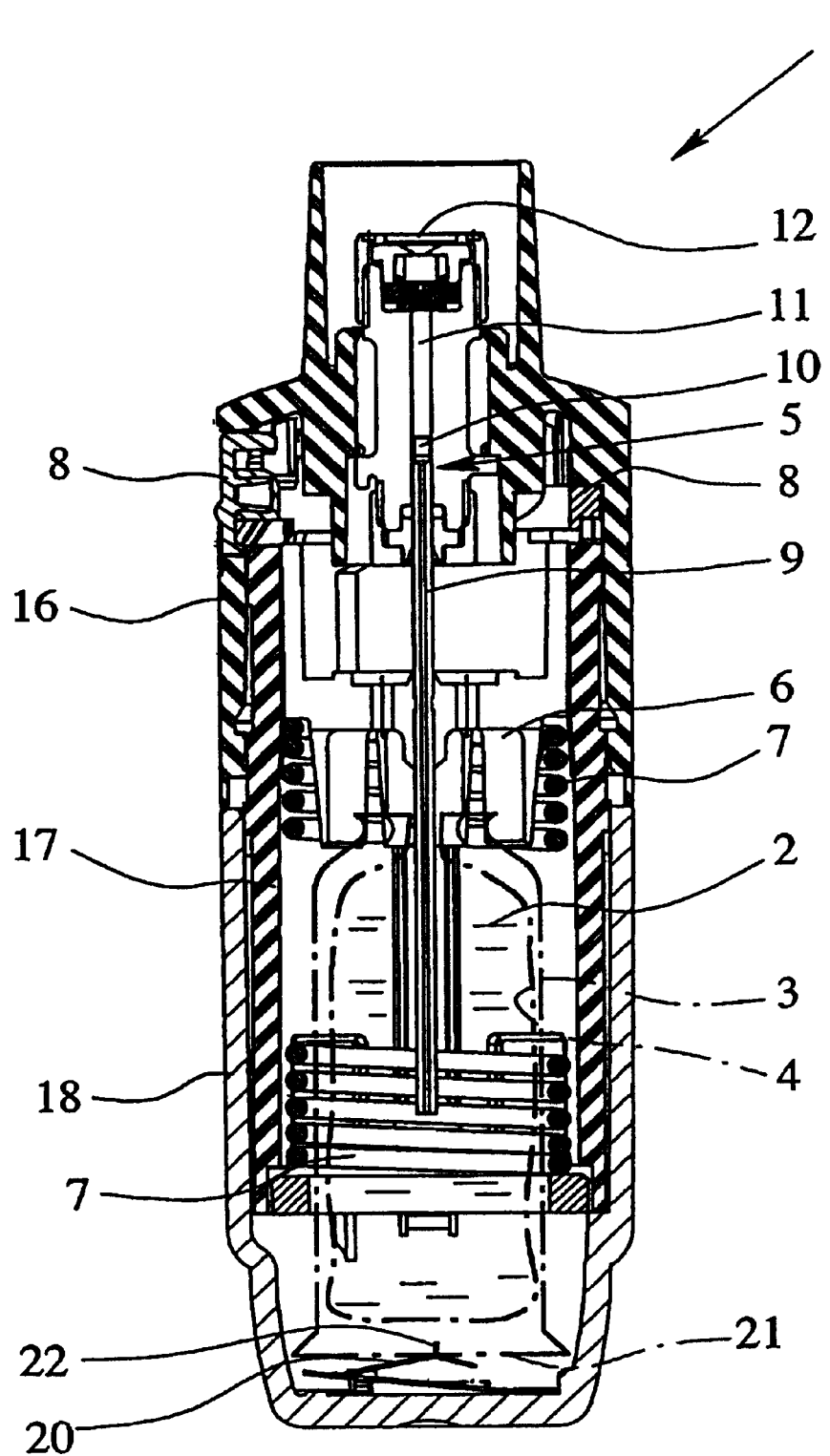
FIG. 2 is a diagrammatic section through the known nebulizer in the tensioned stated, rotated through 90° compared with FIG. 1.

FIGS. 1 and 2 show a known nebulizer 1 for nebulizing a fluid 2, particularly a highly effective pharmaceutical composition or the like, viewed diagrammatically in the untensioned stated (FIG. 1) and in the tensioned state (FIG. 2). The nebulizer is constructed in particular as a portable inhaler and preferably operates without propellant gas.

When the fluid 2, preferably a liquid, more particularly a pharmaceutical composition, is nebulized, an aerosol is formed which can be breathed in or inhaled by a user. Usually the inhaling is done at least once a day, more particularly several times a day, preferably at set intervals.

The nebulizer 1 has an insertable and preferably exchangeable container 3 containing the fluid 2, which forms a reservoir for the fluid 2 which is to be nebulized. Preferably, the container 3 contains an amount of fluid 2 sufficient for multiple use, particular for a given period of administration, such as one month, or for at least 50, preferably at least 100, doses or sprays.

The container 3 is substantially cylindrical or cartridge-shaped and once the nebulizer 1 has been opened the container can be inserted therein from below and changed if desired. It is preferably of rigid construction, the fluid 2 in particular being held in a bag 4 in the container 3.

The nebulizer 1 has a pressure generator 5 for conveying and nebulizing the fluid 2, particularly in a preset and optionally adjustable dosage amount. The pressure generator 5 has a holder 6 for the container 3, an associated drive spring 7, only partly shown, with a locking element 8 which can be manually operated to release it, a conveying tube 9 with a non-return valve 10, a pressure chamber 11 and an expulsion nozzle 12 in the region of a mouthpiece 13.

As the drive spring 7 is axially tensioned the holder 6 with the container 3 and the conveying tube 9 is moved downwards in the drawings and fluid 2 is sucked out of the container 3 into the pressure chamber 11 of the pressure generator 5 through the non-return valve 10. As the expulsion nozzle has a very small cross section of flow and is constructed in particular as a capillary, such a strong throttle action is produced that the intake of air by suction is reliably prevented at this point even without a non-return valve.

During the subsequent relaxation after actuation of the locking element 8 the fluid 2 in the pressure chamber 11 is put under pressure by the drive spring 7 moving the conveying tube 9 back upwards—i.e. by spring force—and is expelled through the expulsion nozzle 12 where it is nebulized, particularly in particles in the micron or nm range, preferably particles destined for the lungs measuring about 5 microns, which form a cloud or jet of aerosol 14, as indicated in FIG. 1. The conveying and nebulizing of the fluid 2 are thus carried out purely mechanically, i.e. without propellant gas and without electricity.

A user can inhale the aerosol 14, while an air supply can be sucked into the mouthpiece 13 through at least one air supply opening 15.

The nebulizer 1 comprises an upper housing part 16 and an inner part 17 which is rotatable relative thereto, on which an in particular manually operable housing part 18 is releasably fixed, particularly fitted on, preferably by means of a retaining element 19. In order to insert and/or replace the container 3 the housing part 18 can be detached from the nebulizer 1.

By manually rotating the housing part 18 the inner part 16 can be rotated relative to the upper housing part 16, by means of which the drive spring 7 can be tensioned in the axial direction by means of a gear acting on the holder 6. During tensioning the container 3 is moved axially downwards until the container 3 assumes an end position as shown in FIG. 2 in the tensioned state. During the nebulizing process the container 3 is moved back into its original position by the drive spring 7.

The housing part 18 preferably forms a cap-like lower housing part and fits around or over a lower free end position of the container 3. As the drive spring 7 is tensioned the container 3 moves with its end portion (further) into the housing part 18 or towards the end face thereof, while an axially acting spring arranged in the housing part 18 comes to bear on the base 21 of the container and pierces the container 3 or a base seal thereon with a piercing element 22 when the container makes contact with it for the first time, to allow air in.

The nebulizer 1 comprises a monitoring device 23 which counts the actuations of the nebulizer 1, preferably by detecting the rotation of the inner part 17 relative to the upper part 16 of the housing. The monitoring device 23 operates purely mechanically in the embodiment shown.

The construction and mode of operation of a proposed nebulizer 1 and a proposed container 3 will now be described in more detail, referring to FIGS. 3 to 17, but emphasising only the essential differences from the nebulizer 1 according to FIGS. 1 and 2. The remarks relating to FIGS. 1 and 2 thus apply accordingly or in a supplementary capacity.

Figure 3:
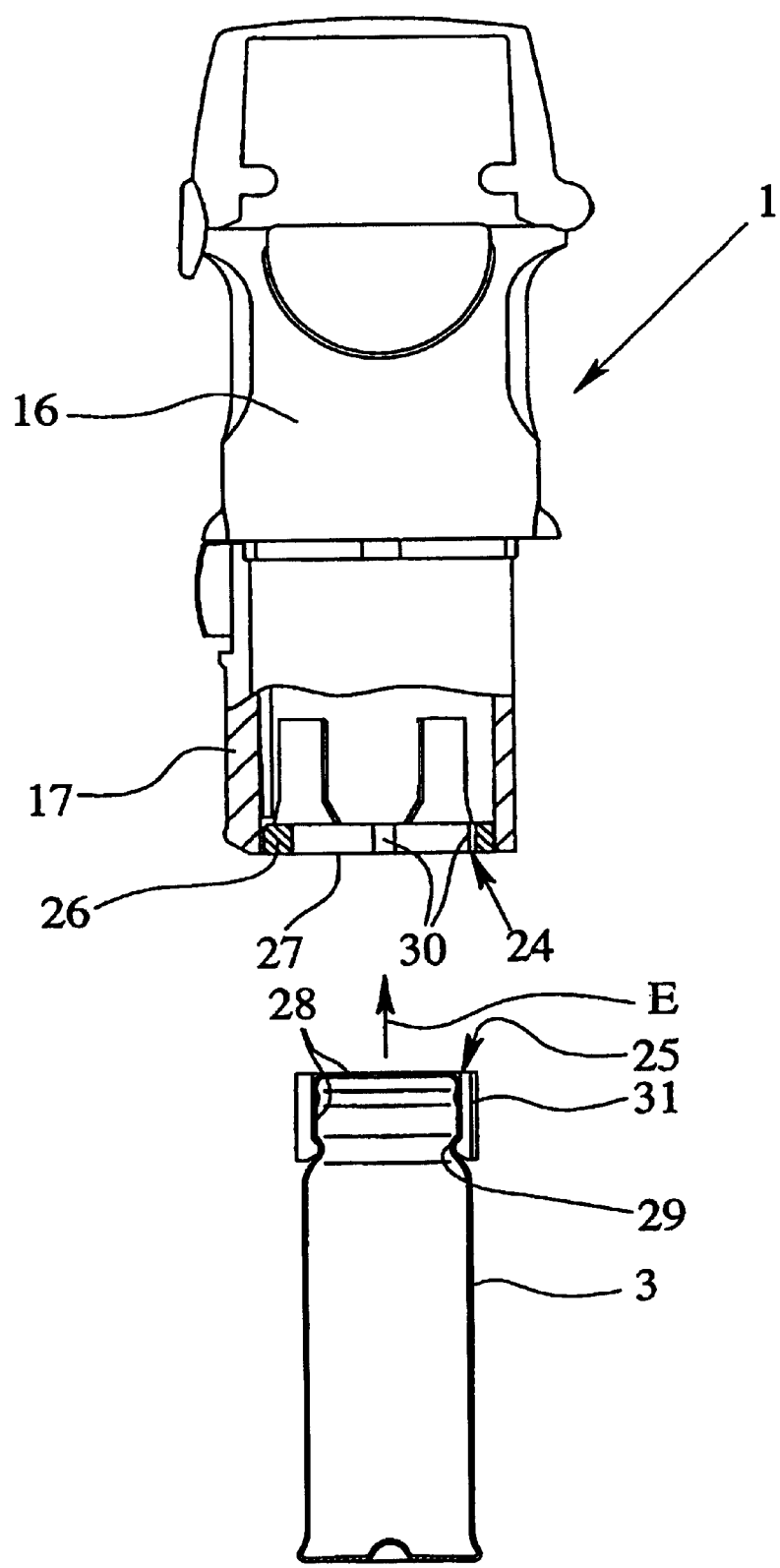
FIG. 3 is a diagrammatic sectional view of a proposed nebulizer and container according to a first embodiment.

FIG. 3 shows, in a diagrammatic partial sectional view, a first embodiment of the proposed nebulizer 1 and container 3. The nebulizer 1 comprises first coding means 24 and second coding means 25 are associated with the container 3.

The coding means 24, 25 cooperates so that the container 3 with the second coding means 25 can only be inserted into the nebulizer 1 or used therewith when the coding means 24, 25 have the appropriate coding. If the appropriate coding is not present, at least the container 3 is prevented from being fully inserted, and particularly the establishing of contact between the fluid 2 and the pressure generator 5 or conveying tube 9 is prevented.

Preferably, the coding means 24, 24 operate or work purely mechanically.

Alternatively or in addition, the coding means 24, 25 may also cooperate or work electrically, inductively, capacitively, magnetically and/or optically, i.e. in particular in contactless manner.

The first coding means 24 are mounted on the nebulizer 1 by interlocking and/or frictional engagement, more particularly as a subsequent addition and/or non-removably. For example, the first coding means 24 may be clicked, clamped, stuck, injection moulded, screwed and/or moulded on to the nebulizer 1 and/or incorporated therein.

In the exemplifying embodiment the first coding means 24 are mounted or formed on a retaining ring 26 of the nebulizer 1. The retaining ring 26 serves as an abutment for the drive spring 7 on the inner part 17 of the nebulizer 1. The retaining ring 26 delimits or defines an insertion opening 27 for the container 3. The insertion opening 27 is formed at the free end of the inner part 17. The container 3 can be inserted into the nebulizer 1 through the insertion opening 27 so that it can be brought into engagement with the holder 6 of the pressure generator 5 and can also be fluidically connected to the pressure generator 5 by the insertion of the conveying tube 9 into the container 3.

In the first embodiment the second coding means 25 are mounted on the container 3 by interlocking and/or frictional engagement, preferably so as to be non removable. For example, the second coding means 25 are clipped, clamped, stuck, injection moulded, screwed and/or moulded on to the container 3 and/or incorporated therein.

In the exemplifying embodiment the second coding means 25 are mounted on a head 28 of the container 3, preferably the second coding means 25 engage in an indentation adjacent to the head 28 or a preferably encircling annular groove 29 in the container 3 for fixing to the container 3.

The seconding means 25 are thus preferably secured to the container 3 by interlocking engagement and preferably so as to be non removable.

In the embodiment shown the container 3 may be inserted in the nebulizer 1—through the insertion opening 27—by a linear movement in the direction of insertion E. If the coding means 24, 25 match, these can be moved past one another for insertion of the container 3 in the first embodiment.

The coding means 24, 25 which operate purely mechanically in the first embodiment preferably comprise projections 30 and/or recesses 31, as additionally shown in the views of the nebulizer 1 from below and of the container 3 from above according to FIGS. 4 and 5 respectively, the combination, number, shape, size, length, width, depth, contour and arrangement thereof—particularly their circumferential position—constituting a coding which is preferably unambiguous. Only when the coding matches can the container 3 with the second coding means 25 be brought into engagement with the first coding means 24 on the nebulizer 1 and accordingly only then can it be inserted into the nebulizer 1 or used therewith.

Figure 4:
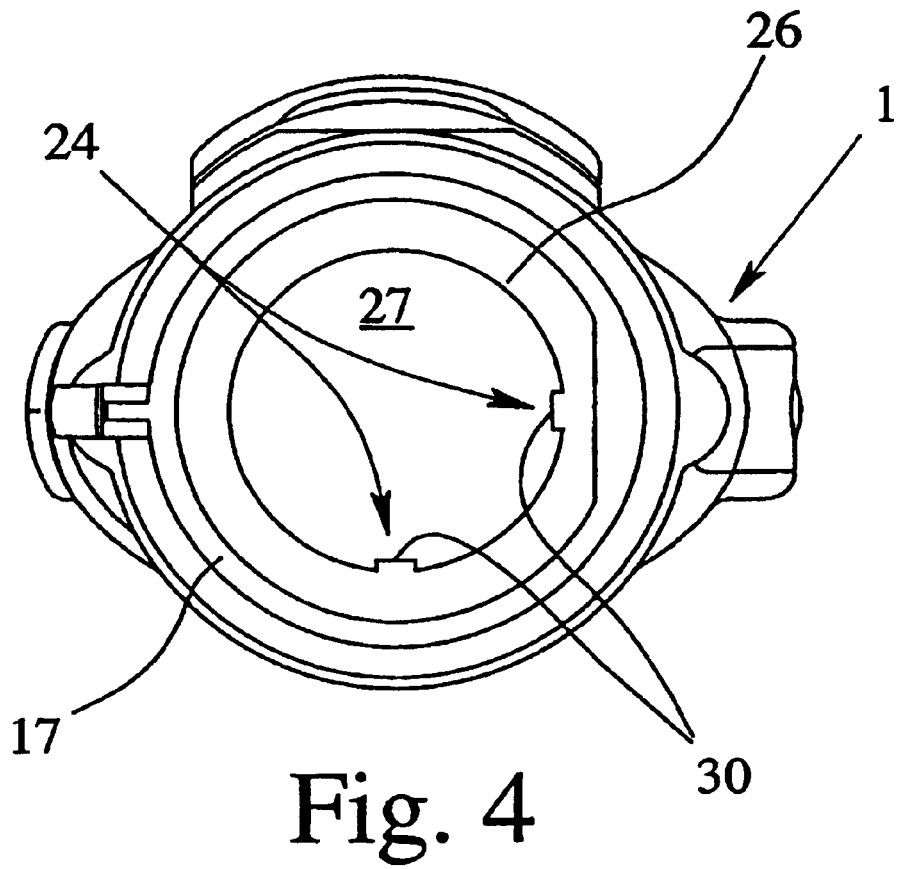
FIG. 4 is a view of the nebulizer in FIG. 3 from below.
Figure 5:
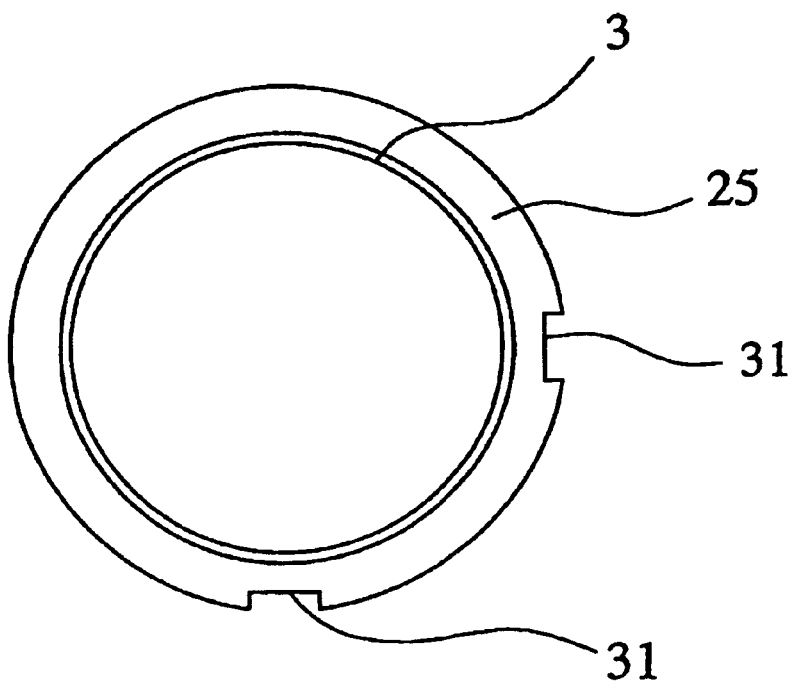
FIG. 5 is a plan view of the container according to FIG. 3.

In the first embodiment the first coding means 24 have two preferably nose-like projections 30 projecting inwardly, i.e. into the insertion opening 27, as is most clearly shown in FIG. 4. The projection 30 thus project at right angles to the direction of insertion E of the container 3.

The projections 30 may if necessary be in the form of a thread or webs or may have any other suitable shape.

In the first embodiment the second coding means 25 preferably comprise two recesses 31 which are formed perpendicularly to the direction of insertion E of the container 3 and are preferably groove-like, particularly extending over the entire axial dimension of the second coding means 25.

In the embodiment shown the projections 30 and the recesses 31 are matched—particularly in their combination, number, shape, size and arrangement—such that the container 3 with the second coding means 25 can be inserted in the retaining ring 26 with the first coding means 24 and past this ring into the nebulizer 1. The coding means 24, 25 thus have codes which fit one another. In particular, the coding means 24, 25 operate on the "lock and key principle".

Preferably, the coding in the first embodiment is provided by a suitable arrangement of the projections 30 and recesses 31 around the circumference, i.e. by a corresponding angular arrangement. This may also be referred to as an angle code, for the sake of simplicity.

Additionally or alternatively coding may also be effected by means of the number and/or shape or size of the projections 30 and recesses 31.

If required, the first coding means 24 may have both at least one projection 30 and one recess 31 and the second coding means 25 may be of complementary construction.

Alternatively or in addition to the linear movement provided in the first embodiment with which the coding means 24, 25 can be made to engage with one another when the codes match, a screwing or rotating movement may also be provided, particularly superimposed thereon.

The projections 30 and/or recesses 31 may be very different in shape. Accordingly, the first and/or second coding means 24, 25 may be, in particularly, in the form of rings, sleeves, brackets, cams, strips, grooves and/or hooks.

Instead of the passing movement of the coding means 24, 25 when the codes match, as envisaged in the first embodiment, during insertion of the container 3, the coding means 24, 25 may also remain in engagement with one another once the container 3 has been inserted, depending on their construction and arrangement.

In the embodiment shown the container 3 is preferably of rotationally symmetrical construction. The second coding means 25 are preferably not rotationally symmetrical in construction. The same then applies to the first coding means 24, to allow matching codes.

The first and/or second means 24, 25 may if necessary be constructed as a separate component—as in the case of the second coding means 25 on the container 3—or may be formed by an existing part—as in the case of the first coding means 24 formed by the retaining ring 26.

The second coding means 25 of the container 3 preferably constitute an unambiguous identification of the container 3, the fluid 2, the concentration of an active substance and/or the amount of fluid in the container 3. This substantially increases safety during use, particularly when similar or even identical container 3 are used for different fluids 2, particularly different pharmaceutical compositions, for different concentrations, e.g. of an active substance, and/or for different amounts of fluid. For example, the containers 3 may be fitted with bags 4 of different capacities. In the description that follows reference will be made only to identifying the pharmaceutical composition or the fluid 2. However, the same also applies to the identification of the container 3 the concentration of active substance and/or the amount of fluid.

In the simplest alternative embodiment the fluid 2 may be identified by having the coding means 25 identify the fluid 2 in a way that is visible to the user, e.g. by the use of colour, script, other symbols or the like.

Preferably, the nebulizer 1 and particularly its monitoring device 23, is constructed so as to allow preferably automatic detection of the identification of the fluid 2 by means of the second coding means 25. In particular, the identification (e.g. a name or other designation of the fluid 2 or pharmaceutical composition) can be stored, displaced or otherwise processed.

Identification of the fluid 2 by the second coding means 25 may be carried out, as selected, by matching the code to the first coding means 24, otherwise detecting the coding of the second coding means 25 and/or independently thereof by means of other suitable identifying means for the coding means 25.

Figure 6:
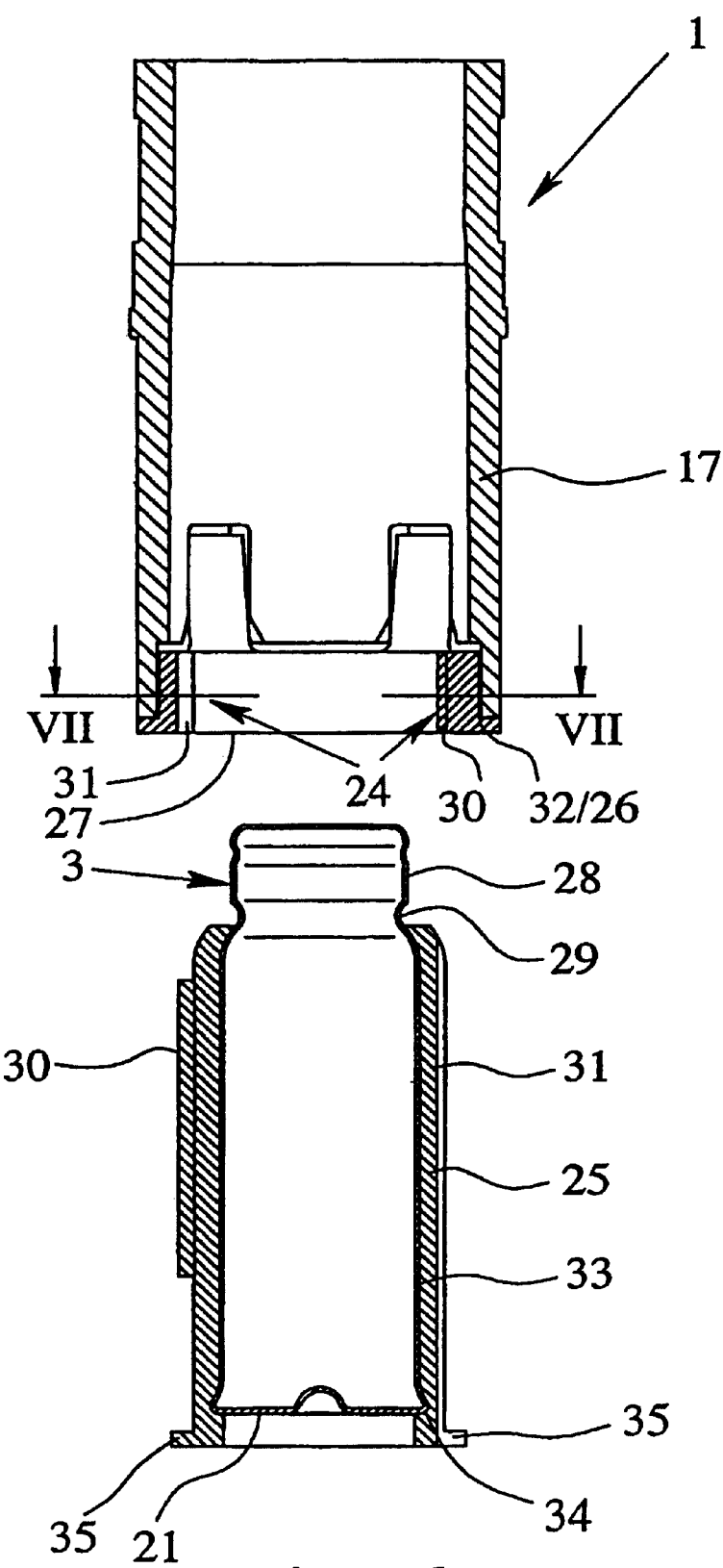
FIG. 6 is a diagrammatic sectional view of a proposed nebulizer and container according to a second embodiment.

The diagrammatic partial section view in FIG. 6 shows a second embodiment of the proposed nebulizer 1 and container 3. In the description that follows, only essential differences from the first proposed embodiment will be described for the second and subsequent embodiment, while the corresponding properties and advantages will become apparent.

In the second embodiment, a push-in portion 32 with the first coding means 24 is provided on the inner part 17 or on the insertion opening 27. The push-in portion 32 may form the retaining ring 26 or may be provided in addition to this or another abutment for the drive spring 7.

Preferably, the push-in portion 32 is only mounted on the nebulizer 1 subsequently, so as to allow the nebulizer to be configured or coded as required. In particular, the mounting of the push-in portion 32 may if necessary be done by the end producer or, for example, at the pharmacy or by a doctor.

The push-in portion 32 can preferably be mounted so as to latch or in some other way fit on the nebulizer 1, particularly the inner part 17. After it has been fitted on, the push-in portion 32 preferably cannot be removed again.

Figure 7:
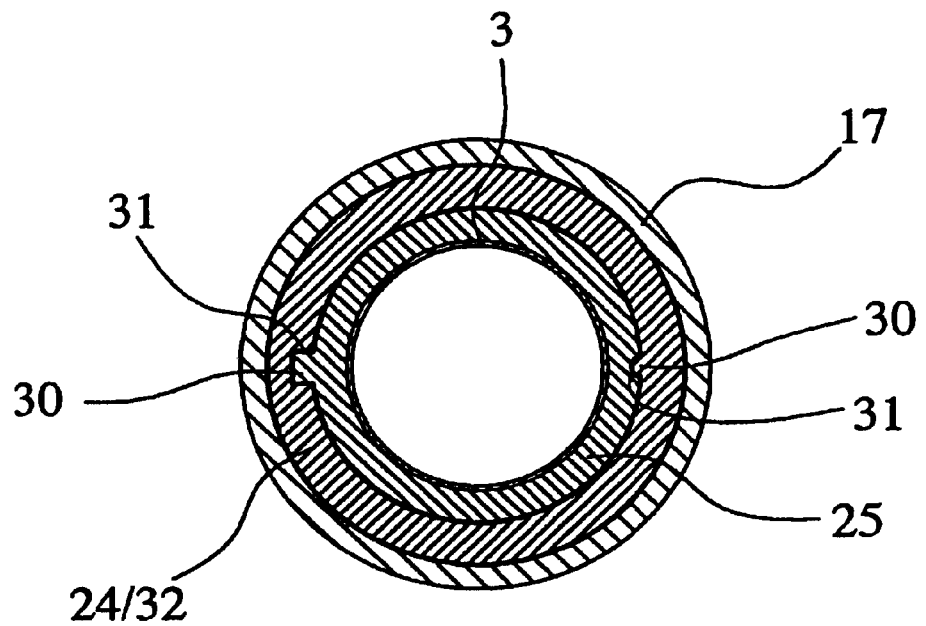
FIG. 7 is a sectional view on the line VII-VII in FIG. 6 with the container inserted.

In the second embodiment the first coding means 24 comprise a recess 31 which is annular or groove-shaped in radial section and a projection 30 which is rounded or nose-shaped in radial section, as is apparent from the sectional view with the container 3 inserted as in FIG. 7.

In the second embodiment the second coding means 25 are preferably in the form of a sleeve and are mounted on an, in particular cylindrical casing 33 of the container 3. In particular, the second coding means 25 surround the casing 23 at least substantially totally peripherally and/or over the entire axial length, as shown in FIG. 6.

In the second embodiment the second coding means 25 engage in the radial indentation or annular groove 29 in the region of the head 28 of the container 3 for axial fixing. Moreover, the second coding means 25 in this case extend beyond the container base 21 and enclose or surround a radially widened end portion or base edge 34 of the container 3.

In particular, the second coding means 25 extend beyond the container base 21 and in the region of this end comprise an annular shoulder 35 or the like which projects radially outwards and forms an insertion stop when inserting the container 3 into the nebulizer 1 in the inserted state and/or a possible handle for the user to hold in order to remove or take out the container 3 from the nebulizer 1.

In the second embodiment the second coding means 25 comprise a groove-shaped or channel-like recess 31 which preferably extends at least substantially over the entire axial length of the second coding means 25 and particularly the container 3.

Furthermore, the second coding means 25 have a preferably web-like projection 30 which also extends in the axial direction over the outer surface of the second coding means 25. In contrast to the recess 31, the projection 30 does not extend over the entire axial length of the second coding means 25 in the embodiment shown, but only over a certain part thereof.

In contrast to the first embodiment, in the second embodiment the first and second coding means 24, 25—at least the right hand projection 30 in FIGS. 6 and 7 and the right hand recess 31—remain in engagement even when the container 3 is fully inserted, in particular they are secured against rotation while being longitudinally displaceable.

As in the first embodiment, the coding means 24, 25 in the second embodiment can also be pushed axially into one another.

In the second embodiment, in addition or alternatively to the angle coding discussed in the first embodiment, length coding may also be provided. For example, the axial position or length of the projection 30 of the second coding means 25 and the axial length of the corresponding recess 31 in the first coding means 24 may vary depending on the code desired, particularly so that if the codes do not match the container 3 with the second coding means 25 at least cannot be fully inserted in the nebulizer 1 or the insertion opening 27 or the first coding means 24, in particular.

It should be noted that the container 3 and/or the second coding means 25, even when the container 3 is fully inserted, may project with its free end out of the nebulizer 1, particularly the inner part 17 or the insertion opening 27, specifically, in the embodiment shown, into the releasable (lower) housing part 18 of the nebulizer.

Figure 9:
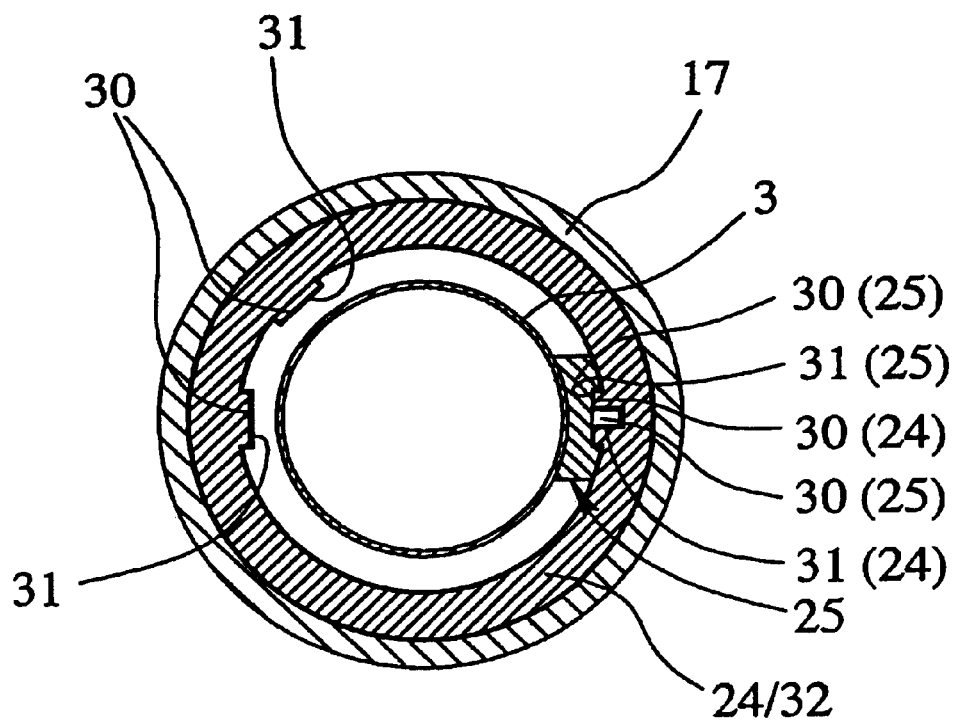
FIG. 9 is a sectional view on the line IX-IX of FIG. 8 with the container inserted.
Figure 8:
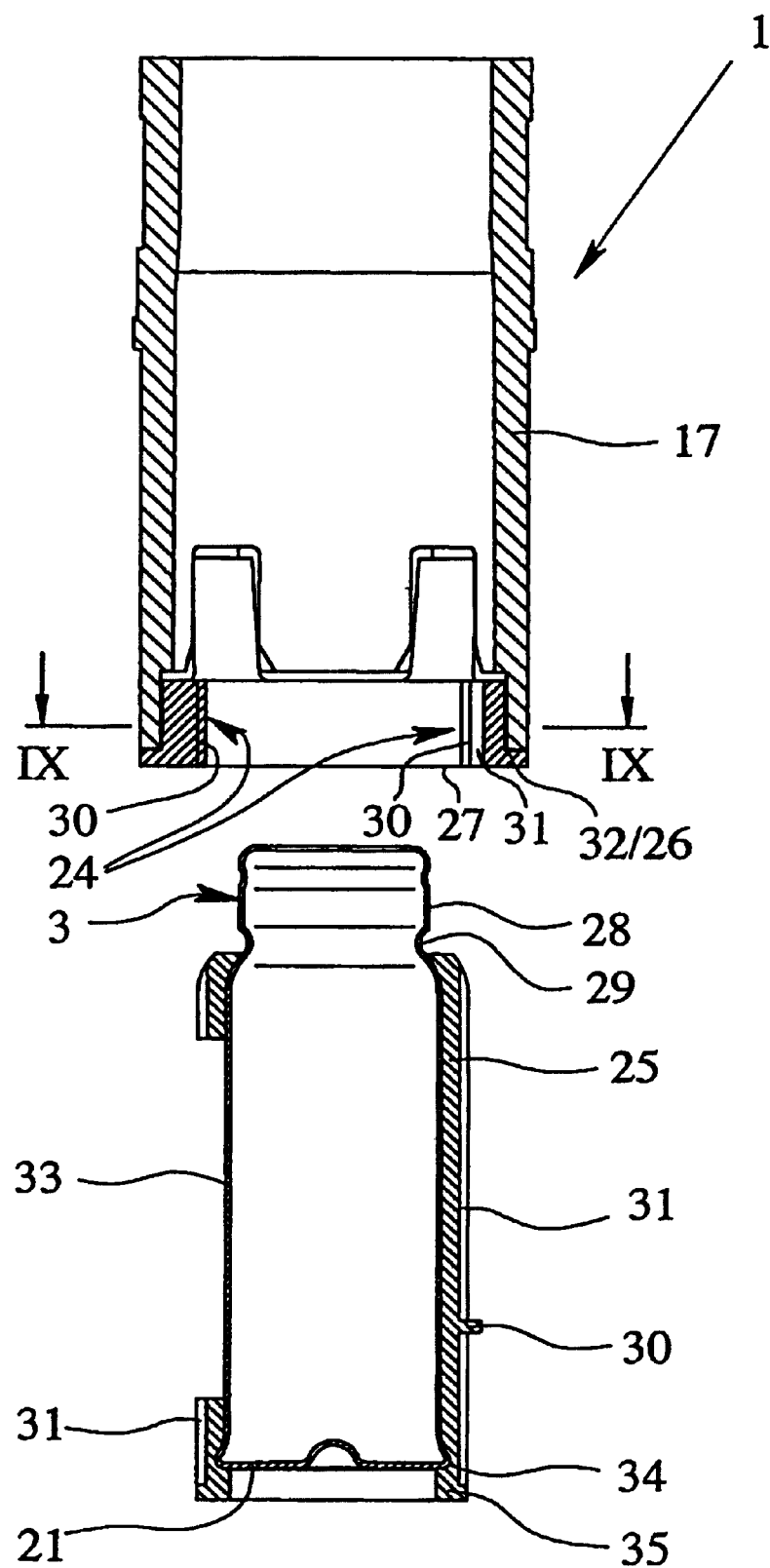
FIG. 8 is a diagrammatic sectional view of a proposed nebulizer and container according to a third embodiment.

In a third embodiment shown in FIGS. 8 and 9 the second coding means 25 on the container 3 are pierced or interrupted in part of the casing, in contrast to the second embodiment. This recess or interruption allows text to be applied, for example, particularly a label or the like, directly on the casing 33 of the container 3, so that the second coding means 25 can be applied to the container 3 independently of this inscription and the inscription remains visible.

The third embodiment, in contrast to the second embodiment, has a somewhat different configuration and arrangement of the projections 30 and recesses 31 of the coding means 24, 25, as can be seen from the sectional view with the container 3 inserted in FIG. 9. The brackets in each case indicates which coding means 24 or 25 are associated with the projections 30 and recesses 31.

In particular, the second coding means 25—in the view shown in FIGS. 8 and 9 on the right hand side—have an at least substantially continuous axial groove as recess 31 and a nose-like projection 30 in this axial group at a specific axial position. The first coding means 24 are accordingly provided with a corresponding recess 31 in a projection 30.

In the third embodiment, there is both an angle code and a length as described above.

Figure 10:
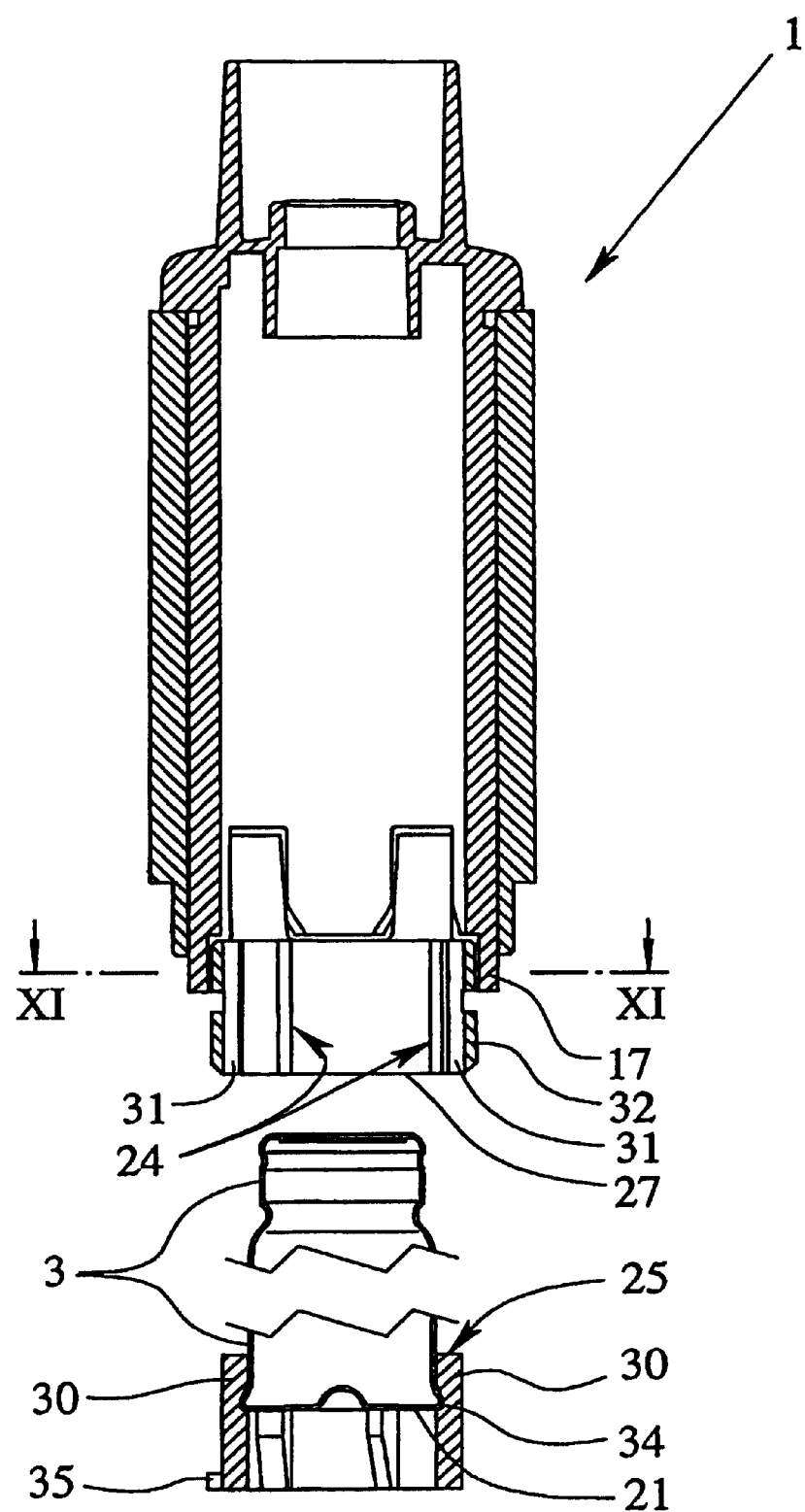
FIG. 10 is a diagrammatic sectional view of a proposed nebulizer and container according to a fourth embodiment.
Figure 11:
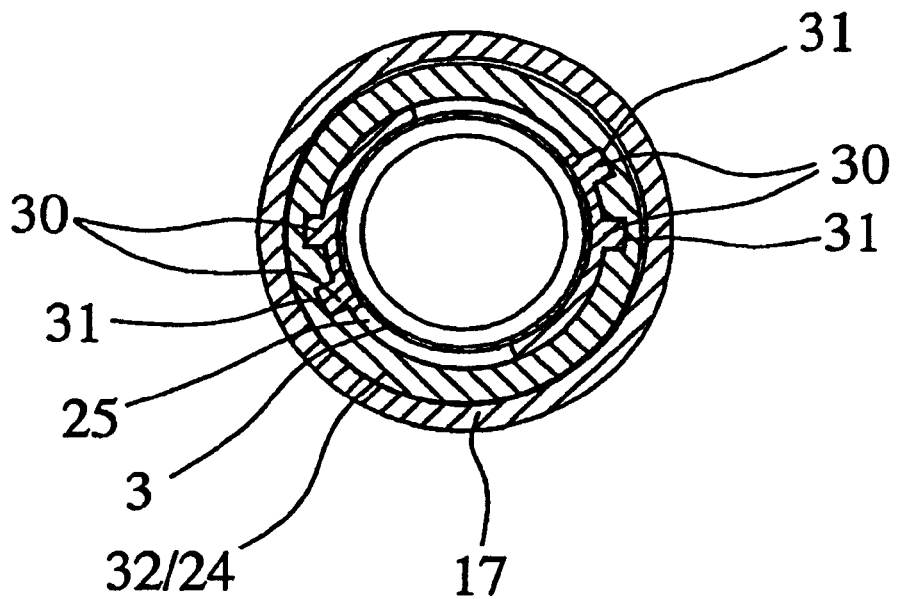
FIG. 11 is a sectional view on the line XI-XI in FIG. 10 with the container inserted.

In a fourth embodiment shown in FIGS. 10 and 11, the second coding means 25 are preferably substantially annular in shape and/or are arranged at the free end of the container 3 or in the region of the container base 21. Preferably, the second coding means 25 in turn surround the, in particular, broadened end portion or base edge 34 of the container 3 and are thus secured to the container 3 by interlocking engagement at least in the axial direction.

The sectional view with the container 3 inserted as shown in FIG. 11 illustrates the configuration and arrangement of the projections 30 and recesses 31 provided in the fourth embodiment.

In the first to fourth embodiments the projections 30 and recesses 31 of the first coding means 24 are preferably arranged on a radial inner surface or constructed to act radially inwards and in the case of the second coding means 25 are accordingly mounted on a radial outer surface or design to act radially outwards. However, this is not absolutely essential. In particular, the mechanism of activity or coding may also be reversed and/or may act in the axial direction or on the end face.

Figure 13:
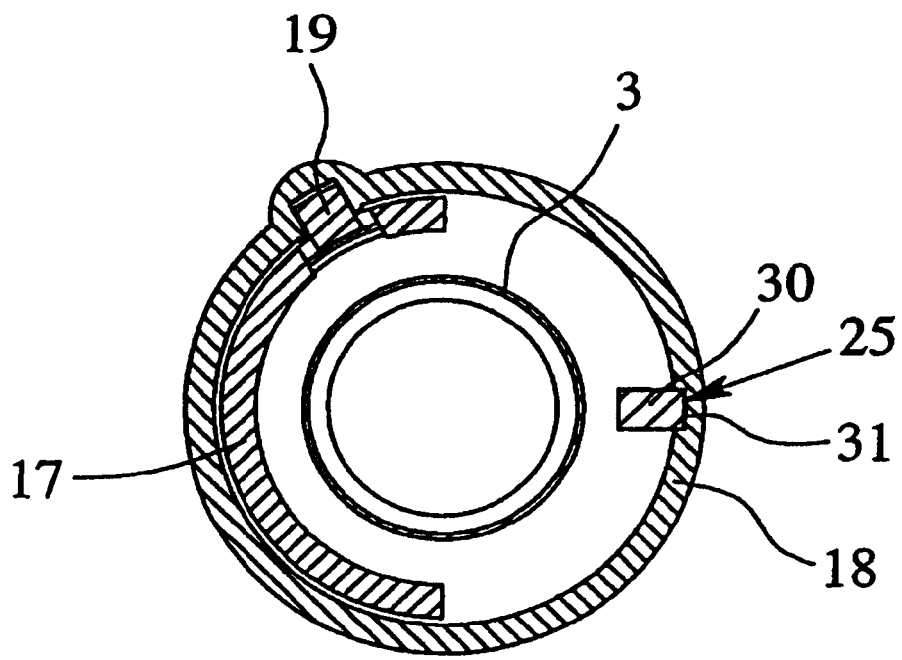
FIG. 13 is a sectional view on the line XIII-XIII in FIG. XII with the container inserted.
Figure 12:
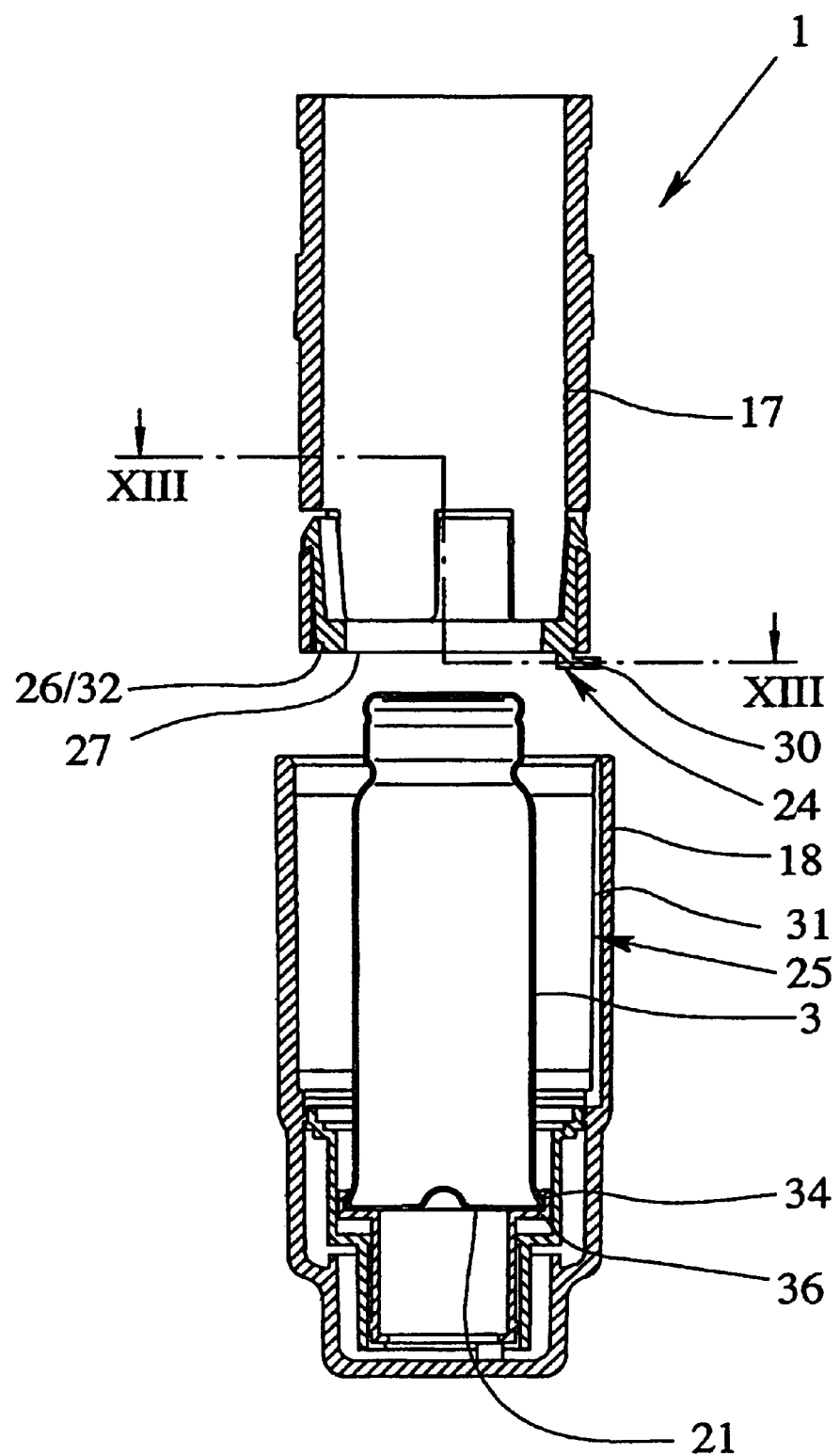
FIG. 12 is a diagrammatic sectional view of a proposed nebulizer and container according to a fifth embodiment.

FIGS. 12 and 13 show a fifth embodiment of the proposed Nebulizer 1 and container 3.

In the fifth embodiment the first coding means 24 are in turn constructed as a push-in portion 32 or arranged thereon the push-in portion 32 preferably being adapted to be mounted in latching and/or non-removable manner on the inner part 17.

The first coding means 24 comprise a radially outwardly protruding projection 30 which projects radially outwards over the inner part 17, in particular. The container 3 is preferably non releaseably attached to the housing part 18, particularly by means of a connecting element 36 which encloses the broadened end portion or base edge 34 of the container 3 by interlocking engagement.

In the fifth embodiment, in contrast to the first to fourth embodiments, the second coding means 25 are preferably formed on a housing portion which is connectable to the nebulizer 1, in this case the (lower) housing part 18 of the nebulizer 1, or is formed thereby.

In particular, the second coding means 25 in the fifth embodiment comprise a radially inwardly open recess 31 extending axially and preferably formed on the inside of the outer wall of the housing part 18.

When the coding means 24, 25 match, during the assembly of the nebulizer 1—i.e. when the lower housing part 18 is being fitted together with the container 3—the projection 30 of the first coding means 24 can be engaged or pushed into the recess 31 of the second coding means 25, as indicated in FIG. 13 with the inserted container 3 or the assembled housing part 18. If the codes do not match, on the other hand, the housing part 18 is prevented from being mounted on the nebulizer 1, and in particular from being pushed on to the inner part 17.

Instead of the preferred non removable connection of the (lower) housing part 18 to the container 3, a coding of the kind described may also be provided between them so that the container 3 can only be inserted in the (lower) housing part 18 when the codes match.

Figure 14:
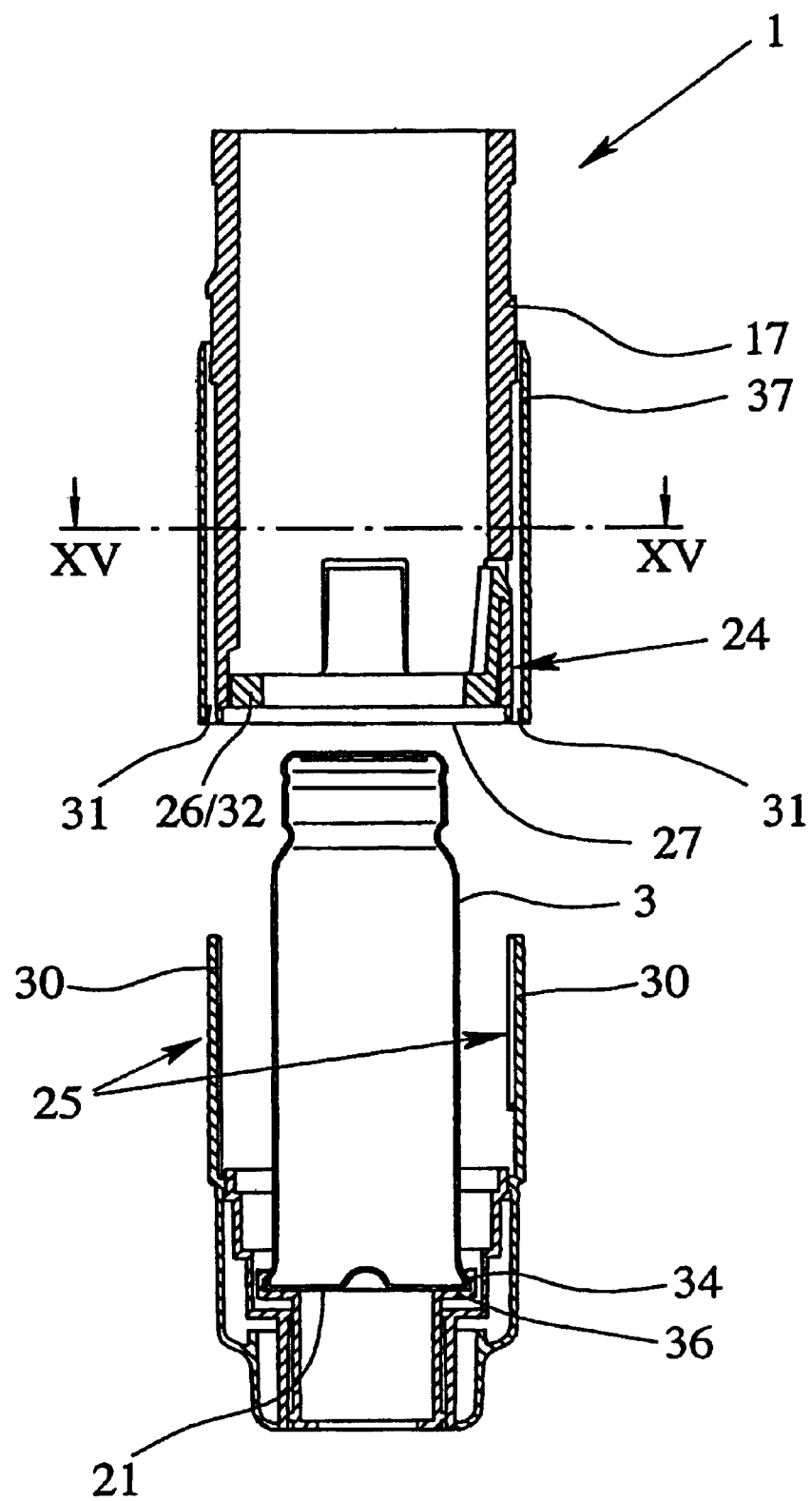
FIG. 14 is a diagrammatic sectional view of a proposed nebulizer and container according to a sixth embodiment.
Figure 15:
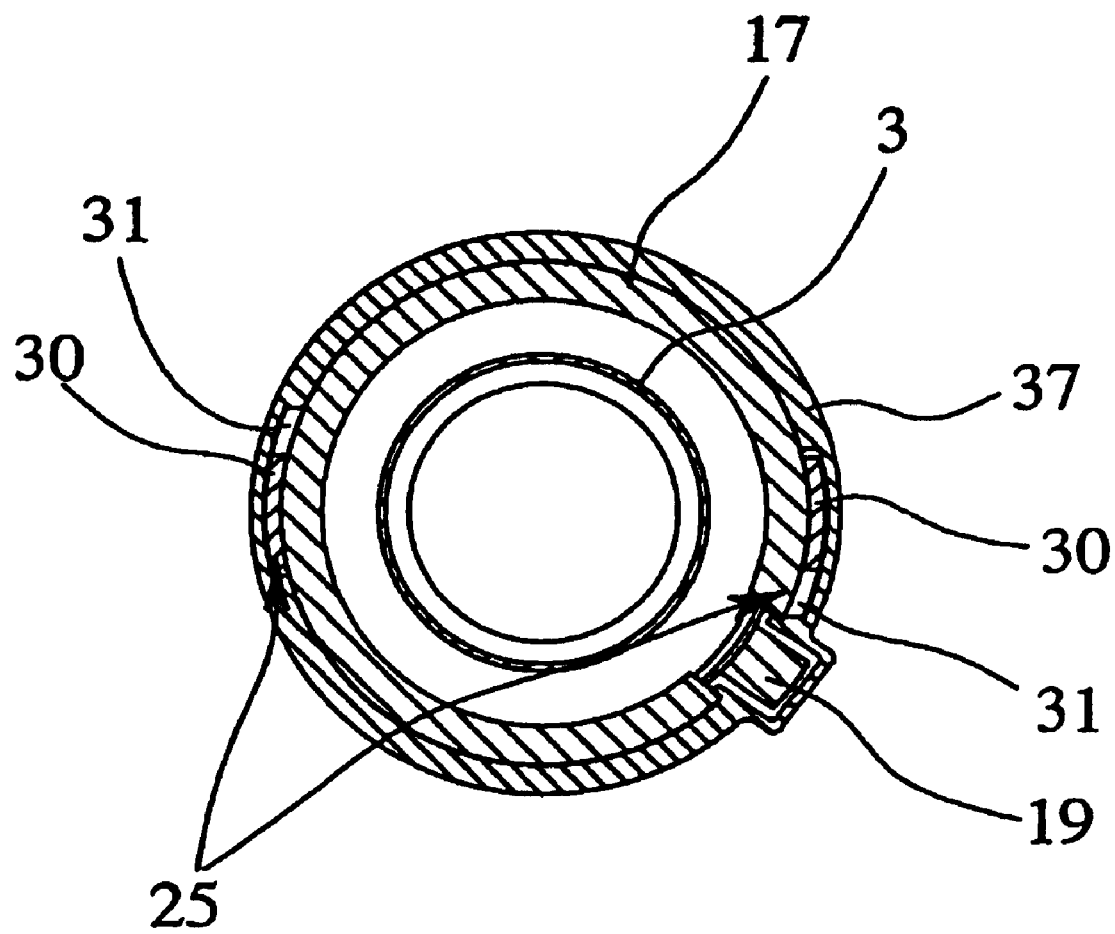
FIG. 15 is a sectional view on the line XV-XV in FIG. 14 with the container inserted.

FIGS. 14 and 15 show a sixth embodiment of the proposed nebulizer 1 and container 3, wherein FIG. 14 does not show the housing part 18 and FIG. 15 shows the inserted or assembled state.

In contrast to the fifth embodiment, the housing part 18 can be mounted or fixed on the nebulizer 1 or on the inner part 17 thereof by a bayonet type fitting, particularly with a combined and/or superimposed linear and rotary movement. For this purpose the first coding means 24 preferably comprise a connecting sleeve 37 which is adapted to be mounted or is already mounted on the nebulizer 1 or on the inner part 17 thereof. The second coding means 25 comprise arm-like projections, preferably in the form of hooks at the free end, which allow the bayonet-like fitting of the housing part 18 to the nebulizer 1 when the codes match by engaging in the correspondingly shaped recesses 31.

The recesses 31 of the first coding means 24—particularly on the connecting sleeve 37—are preferably substantially slot-like in construction in the sixth embodiment and are preferably undercut so that in the assembled state it is impossible for the housing part 18 to be pulled away axially, thanks to interlocking engagement with the arm-like projections 30 of the second coding means 25.

In the embodiment shown the projections 30 of the second coding means 25 engage in the recesses 31, preferably in the region of the inside of the connecting sleeve 37, such that the connecting sleeve 37 during the mounting of the housing part 18 on the nebulizer 1 engages or is pushed into the gap or annular space between the projections 30 of the second coding means 25 and the inner wall of the preferably at least substantially cylindrical portion of the housing part 18.

Figures 16, 17:
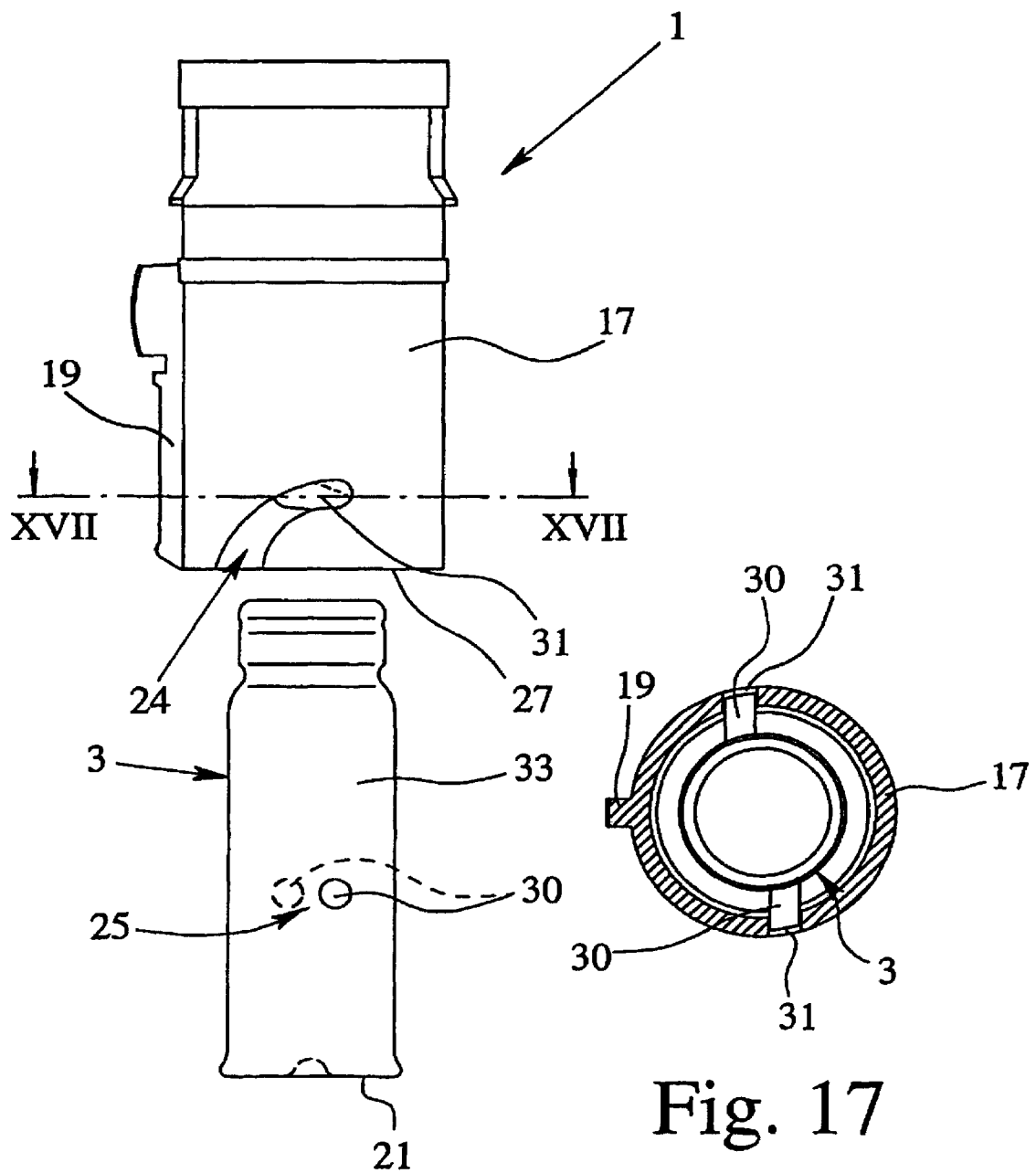
FIG. 16 is a diagrammatic sectional view of a proposed nebulizer and container according to a sixth embodiment.
FIG. 17 is a sectional view on the line XVII-XVII in FIG. 16 with the container inserted.

FIGS. 16 and 17 show a seventh embodiment of the proposed nebulizer 1 and container 3. The seventh embodiment resembles the sixth embodiment. For mounting the housing part 18, in this case a screw-like movement of the housing part 18 with the container 3 relative to the nebulizer 1, particularly the inner part 17 thereof, is envisaged, in particular.

The nebulizer 1 or the inner part 17 comprises the first coding means 24, specifically slot-like recesses 31 preferably extending substantially at an angle and bent in or on the inner part 17.

The second coding means 25 arranged on the housing part 18 or directly on the container 3 comprise, in the seventh embodiment, preferably knob-like projections 30 adapted to the recesses 31 of the first coding means 24, so that when the codes of the coding means 24, 25 fit the housing part 18 together with the container 3 can be mounted on the nebulizer 1 by a screw-like motion, as indicated in FIG. 17 without the housing part 18.

Instead of or in addition to a knob-like construction on the outer surface 33, the projections 30 may also be of a suitable finger-like or arm-like construction when the recesses 31 are of corresponding configuration and thus engage in the recesses 31 when the codes match.

A particular advantage of the present invention resides in the fact that the first and/or second coding means 24, 25 can be added subsequently, so that for example the nebulizer 1 and/or the container 3 can be coded as later as possible during the manufacturing process and the coding is freely selectable and thus finally fixed. Alternatively or in addition, the coding can be selected at the start and finally fixed at that point.

According to an alternative embodiment, the coding means 24, 25 may be constructed so that the coding of the first coding means 24 is automatically fixed only when the container 3 is inserted in the nebulizer 1 for the first time, e.g. by irreversible deformation or by the breaking off of engaging elements or the like.

If required, the coding means 24, 25 may each have projections 30, recesses 31 or the like arranged in different planes and/or axial positions in the direction of insertion.

The embodiments described hereinbefore, especially individual elements and aspects of the embodiments, may be combined with one another and/or reversed in their kinematic operation, as necessary. In particular, the number and arrangement of the projections 30 and recesses 31 may be varied as necessary and adapted to the particular conditions.

We claim:

1. A nebulizer for a fluid, comprising:
a manually operable, purely mechanical nebulizer body,
means for conveying and nebulizing of the fluid, and
a replaceable container of the fluid for use in the nebulizer body,
wherein a first coding is provided on the nebulizer body and a second coding is provided on the container,
wherein the first and second codings cooperate with each other in a manner such that only a container with the correct second coding is usable with the container body,
wherein one of said first and second codings is a projection and the other of said first and second codings is a recess, said projection and recess extending in an insertion direction of the container into the nebulizer body for engagement by axial insertion of the container; and
wherein said container is fully insertable into the nebulizer body only when the shape and size of the projection is matched to the shape and size of said recess.

2. The nebulizer for a fluid according to claim 1, wherein said codings are one of a plurality of different codings of varying axial length.

3. The nebulizer for a fluid according to claim 1, wherein the means for conveying and nebulizing of the fluid are purely mechanical.

4. The nebulizer for a fluid according to claim 1, wherein the second coding is located on an end of the container.

5. The nebulizer according to claim 1, wherein the first and second codings are constructed so that when the codings do not match at least the container is prevented from being fully inserted to an extent precluding discharging of the contents of the container by a pressure generator of the nebulizer body.

6. The nebulizer according to claim 1, wherein the first coding is arranged on or in a region of an opening for insertion of the container into nebulizer.

7. The nebulizer according to claim 1, wherein the first coding is arranged on or in a region of a holder of the nebulizer for the container.

8. The nebulizer according to claim 1, wherein the second coding corresponds to one of the fluid in the container, a concentration of active substance in the fluid or an amount of fluid in the container.

9. The nebulizer according to claim 1, wherein the second coding is mounted on the container in frictional or interlocking engagement.

10. The nebulizer according to claim 1, wherein the second coding is arranged on a head of the container.

11. The nebulizer according to claim 10, wherein the container comprises, adjacent to the head, a radial indentation in which the second coding engages for fixing to the container.

12. The nebulizer according to claim 1, wherein the second coding is mounted on a cylindrical casing of the container.

13. The nebulizer according to claim 4, wherein the second coding is arranged on a base of the container.

14. The nebulizer according to claim 13, wherein the container has a radially widened end portion which is surrounded by the second coding for fixing to the container.

15. A nebulizer for a fluid, comprising:
a nebulizer body comprised of a pair of axially separable body parts,
means for conveying and nebulizing of the fluid, and
a replaceable container of the fluid for use in the nebulizer body, the container being axially insertable and removable from within said body parts when the body parts are separated,
wherein a first coding is provided in one the nebulizer body parts and a second coding is provided on an end of the container, said first and second codings being engageable by linear relative movement therebetween,
wherein the first and second codings cooperate with each other on axial insertion of the container into the body parts in a manner such that only a container with the correct second coding is usable with the container body, said body parts being rejoinable with the container in an operable position only when the shape and size of the first coding matches the shape and size of the second coding.

16. The nebulizer for a fluid according to claim 15, wherein said codings are one of a plurality of different codings of varying axial length.

17. The nebulizer according to claim 15, wherein the first coding is arranged on or in a region of an opening for insertion of the container into nebulizer.

18. The nebulizer according to claim 15, wherein the first coding is arranged on or in a region of a holder of the nebulizer for the container.

19. The nebulizer according to claim 15, wherein the second coding corresponds to one of the fluid in the container, a concentration of active substance in the fluid or an amount of fluid in the container.

20. The nebulizer according to claim 15, wherein the second coding is arranged on a head of the container and wherein the container comprises, adjacent to the head, a radial indentation in which the second coding engages for fixing to the container.

* * * * *